(12) United States Patent
Hamblin (10) Patent No.: US 11,337,731 B1
(45) Date of Patent: May 24, 2022

(54) LUBE DISTRIBUTION APPARATUS FOR USE WITH SPERM COLLECTION DEVICE

(71) Applicant: William Hamblin, Norris City, IL (US)

(72) Inventor: William Hamblin, Norris City, IL (US)

(*) Notice: Subject to any disclaimer, the term of this patent is extended or adjusted under 35 U.S.C. 154(b) by 0 days.

(21) Appl. No.: 17/270,285

(22) PCT Filed: Sep. 9, 2020

(86) PCT No.: PCT/US2020/049816
§ 371 (c)(1),
(2) Date: Feb. 22, 2021

(87) PCT Pub. No.: WO2021/158258
PCT Pub. Date: Aug. 12, 2021

Related U.S. Application Data (60) Provisional application No. 62/970,213, filed on Feb. 5, 2020.

(51) Int. Cl.
*A61F 5/00* (2006.01)
*A61B 17/43* (2006.01)
*A61B 17/00* (2006.01)

(52) U.S. Cl.
CPC .... *A61B 17/43* (2013.01); *A61B 2017/00849* (2013.01)

(58) Field of Classification Search
CPC .............. A61F 5/0096; A61B 10/0058; A61B 10/0045; A61B 17/43; A61B 2017/00849; A61H 19/32; A61H 9/005; A61H 19/40; A61M 35/003
See application file for complete search history.

(56) References Cited

U.S. PATENT DOCUMENTS

| | | | |
|---|---|---|---|
| 4,735,751 A | 4/1988 | Guntly | |
| 5,232,664 A | 8/1993 | Krawzak et al. | |
| 5,503,627 A | 4/1996 | McKinnon et al. | |
| 5,782,818 A | 7/1998 | Shubin | |
| 7,163,508 B1* | 1/2007 | Washington | A61H 21/00 600/38 |
| 7,753,895 B2 | 7/2010 | Matsuura | |
| 8,475,422 B2* | 7/2013 | Wu | A61F 5/453 600/38 |

(Continued)

*Primary Examiner* — Samuel G Gilbert
(74) *Attorney, Agent, or Firm* — Martin IP Law Group; C. Richard Martin (57) ABSTRACT

A lube distribution apparatus for use in connection with a sperm collection device is provided and configured to be installed on the sperm collection device in lieu of the end cap. The lube distribution apparatus comprising a main body having a cylindrical opening at a first end thereof, the cylindrical opening having means for engaging an open end of the sperm collection device. A lubricant reservoir is located within the main body of the lube distribution device for housing lubricant to be used in the sperm collection device. Injection means are provided for injecting lubricant from the lubricant reservoir into the sperm collection device. The lube distribution apparatus may further include an end cap removably affixed to a second end of the main body and enclosing the lubricant reservoir. A vent for allowing outside air to enter the lubricant reservoir during actuation of the injection means may also be provided. The vent may be located in the end cap or, alternatively, directly in the main body of the lube distribution device.

10 Claims, 12 Drawing Sheets

(56) References Cited

U.S. PATENT DOCUMENTS

| | | |
|---|---|---|
| 10,342,731 B2 | 7/2019 | Cambridge |
| 2004/0127766 A1* | 7/2004 | Chen ...................... A61H 19/44 600/38 |
| 2012/0215189 A1 | 8/2012 | Wu |
| 2015/0034504 A1 | 2/2015 | Clayton |

* cited by examiner

LUBE DISTRIBUTION APPARATUS FOR USE WITH SPERM COLLECTION DEVICE

BACKGROUND OF THE INVENTION

Field of the Invention

The present invention relates to accessories for use in connection with devices for discreet and camouflaged collection of sperm from human males. More specifically, the present invention relates to a device that can be quickly and easily attached to the end of a flashlight shaped sperm collection device that is designed to inject a lubricant into the interior of the sperm collection device.

Description of the Related Art

Figure 1:
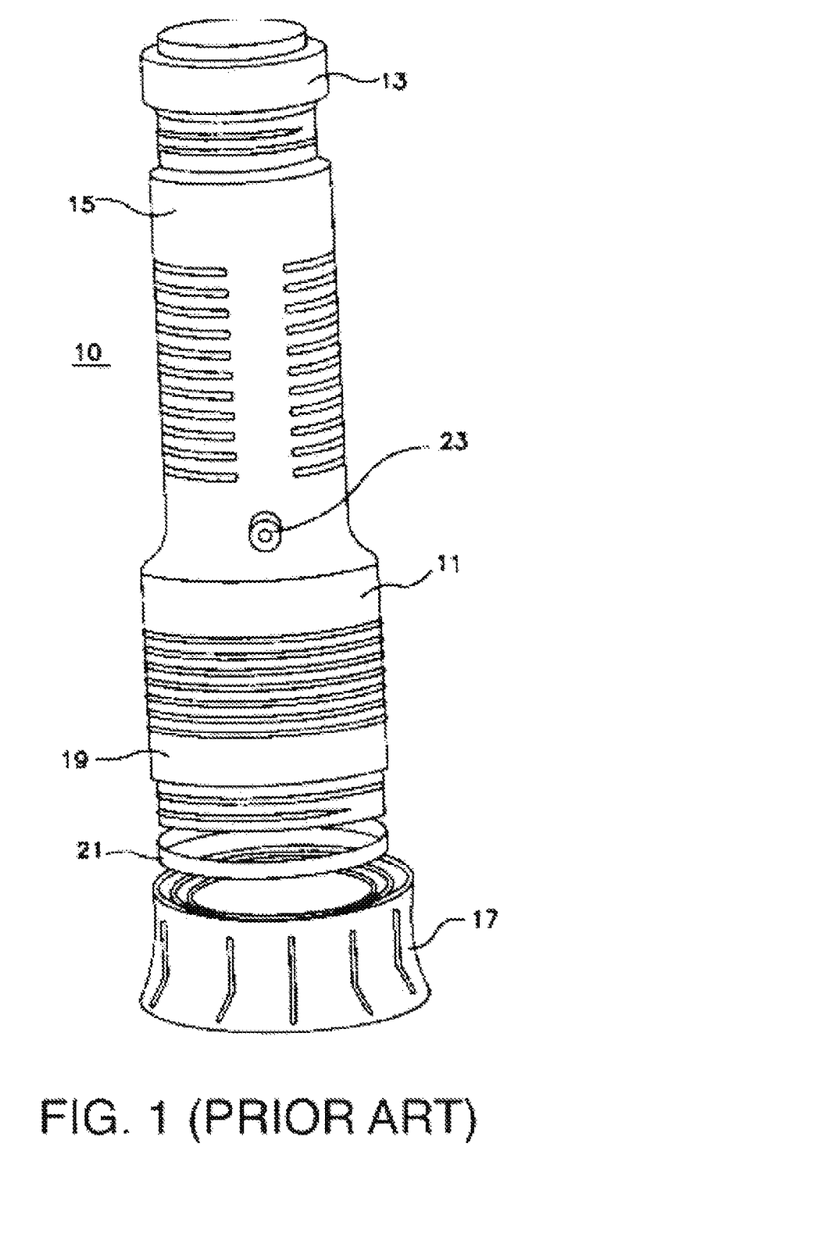
FIG. 1 is a perspective view of a PRIOR ART device useful for collection of sperm from human males shown with a simulated lens cap.
Figure 2:
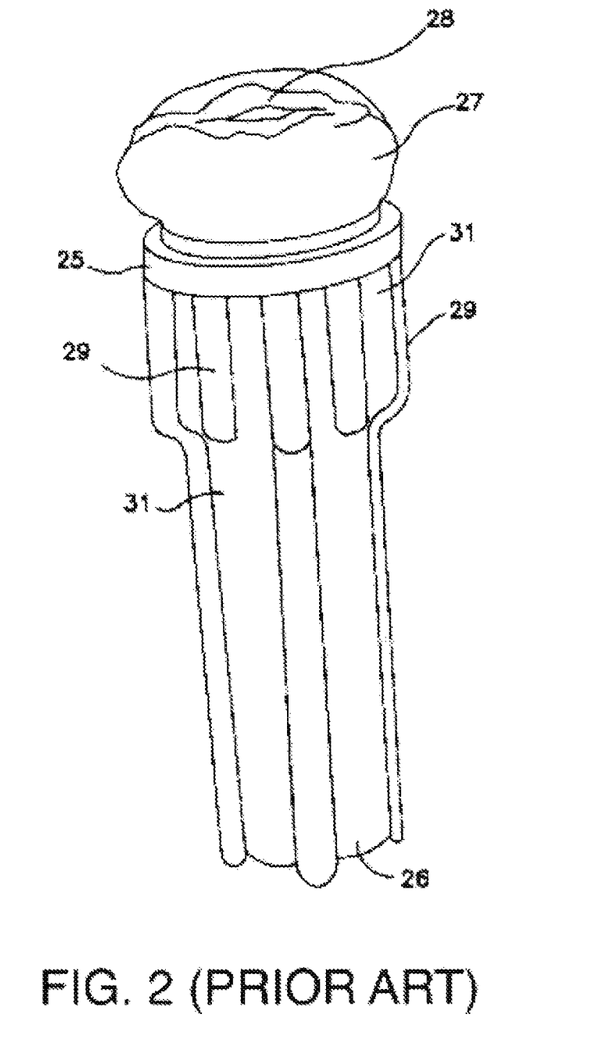
FIG. 2 is a perspective view of the PRIOR ART device shown in FIG. 1 with a simulated human female orifice insert installed in place of the simulated lens cap.

U.S. Pat. No. 5,782,818 describes a device useful for collection of sperm from human males, preferably in a discreet, camouflaged manner. As shown in FIG. 1 and FIG. 2, the device 10 has an outer shell, in this case as a flashlight 11, having a generally tubular inside chamber and an exterior with the appearance of an ordinary device normally found in a public environment. Flashlight 11 includes a first end cap 13 that is threaded on to small end 15. A simulated lens cap end 17 also threads onto flashlight 11 at the large end 19, and may included an o-ring 21 or other fluid sealing means. To be used as a sperm collection device, the simulated lens cap end 17 is removed and an insert 25 insert formed from an elastomeric gel having the general tactile feel of human flesh is inserted in its place. One end 27 of the insert has an opening simulating a body orifice. The insert includes a central passage sized to accommodate a human male sex organ in said opening while providing at least a cushioning amount of the elastomeric gel.

One problem associated with this device is the lack of lubrication. Friction between the insert opening and the human male sex organ can cause discomfort, irritation, and possibly burns to the skin of the male sex organ. Lubricant could be added through the insert opening. However, that requires an interruption of the experience and can be messy.

Accordingly, there is a need for an effective and easy way to provide a lubricant between the insert opening and the human male sex organ through an opening other than the one in which the human male sex organ is to be inserted. Such a device would reduce the mess of injecting lubricant directly into that opening and also avoid the necessity of interrupting the experience to apply lubricant.

SUMMARY OF THE INVENTION

It is therefore an object of the present invention to provide a device that will inject (spray, Squirt) lube into the center of the inner chamber of a sperm collection device to provide lubrication to help with the overall usability of said sperm collection device in many ways.

It is also an object of the invention to provide lubricant to the inner surfaces of a sperm collection device at the push of a button with minimal effort from the user.

A further object of the invention is to provide lube without having to remove the human male sex organ from the sperm collection device during use.

Another object of the invention it to have a refillable lubricant/fluid reservoir to hold the lube until it is ready to be used, and for that reservoir to be easy to fill cleanly with less spillage.

It is a further object of the invention to provide a lube distribution apparatus that can be readily attached to a number of different sperm collection devices that are currently available, and to provide a device that is either permanently attached to the sperm collection device, or one that can be quickly and easily attached to and detached from a sperm collection device.

Another object of the invention is to be able to use different attachments in conjunction with this lube dispensing device, and a device that can be used with almost any type of lubricant that is commercially available.

A further object is to provide a lube distribution apparatus that is easily repairable with parts that are already on the market and easy to access, resulting in increased life span of the sperm collection device by cutting down on friction and heat by having lubrication as needed on demand.

According to one presently preferred embodiment of the invention, there is provided a lube distribution apparatus for use in connection with a sperm collection device and configured to be installed on the sperm collection device in lieu of the end cap. The lube distribution apparatus comprising a main body having a cylindrical opening at a first end thereof, said cylindrical opening having means for engaging an open end of the sperm collection device, a lubricant reservoir located within said main body for housing lubricant to be used in the sperm collection device; and injection means for injecting lubricant from the lubricant reservoir into the sperm collection device. The lube distribution apparatus may further include an end cap removably affixed to a second end of said main body and enclosing said lubricant reservoir.

The injection means of the lube distribution apparatus may include a first opening in fluid communication with the lubricant reservoir; an injector tip projecting from the first end of the main body, said injector tip having a second opening therein; a fluid passageway connecting said first opening to said second opening; and a primer purge pump assembly connected to said fluid passageway for effecting transfer of fluid from the lubricant reservoir to the injector tip. A first fluid passageway may be provided connecting the first opening in the lubricant reservoir to an inlet opening in a primer purge pump. A second fluid passageway may also be provided connecting the second opening in the injector tip to an outlet opening in said primer pump. The primer purge pump may further include an inlet check valve associated with the inlet opening; an outlet check valve associated with the outlet opening; and a purge bulb covering the inlet opening and the outlet opening creating a compressible chamber in fluid communication with the inlet opening and the outlet opening.

A vent for allowing outside air to enter the lubricant reservoir during actuation of the injection means may also be provided. The vent may be located in an end cap removably affixed to a second end of said main body and enclosing said lubricant reservoir. The vent further may further include an opening in the cap that exposes the interior of the lubricant reservoir to outside air, and a check valve located in the opening to control the flow of air from outside into the lubricant reservoir. The check valve may be a Schrader valve. The vent may be disposed in a bushing that is removably secured to an opening in said end cap.

Alternatively, the vent may further comprise an opening in an outer surface of the main body in fluid communication with the outside air, an opening in fluid communication with the lubricant reservoir; a fluid passage connecting the first opening to the second opening; and a check valve located in said opening to control the flow of air from outside into the lubricant reservoir. In this configuration, the check valve may also be a Schrader valve.

These and other objects, features and advantages of the present invention will become apparent from a review of the following drawings and detailed description of the preferred embodiments of the invention.

BRIEF DESCRIPTION OF THE DRAWINGS

The present invention can best be understood in connection with the accompanying drawings. It is noted that the invention is not limited to the precise embodiments shown in the drawings, in which.

DETAILED DESCRIPTION OF THE INVENTION

For purposes of promoting and understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

Figure 3:
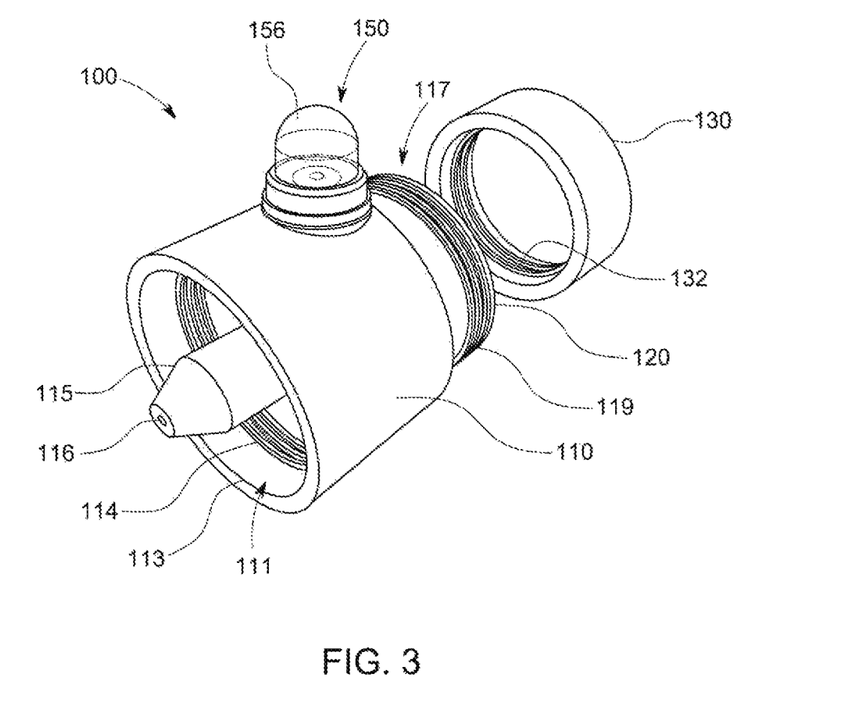
FIG. 3 is an exploded perspective view of the lube distribution apparatus for use with a sperm collection device such as the one shown in FIG. 1 and FIG. 2, according to one preferred embodiment of the invention.
Figure 4:
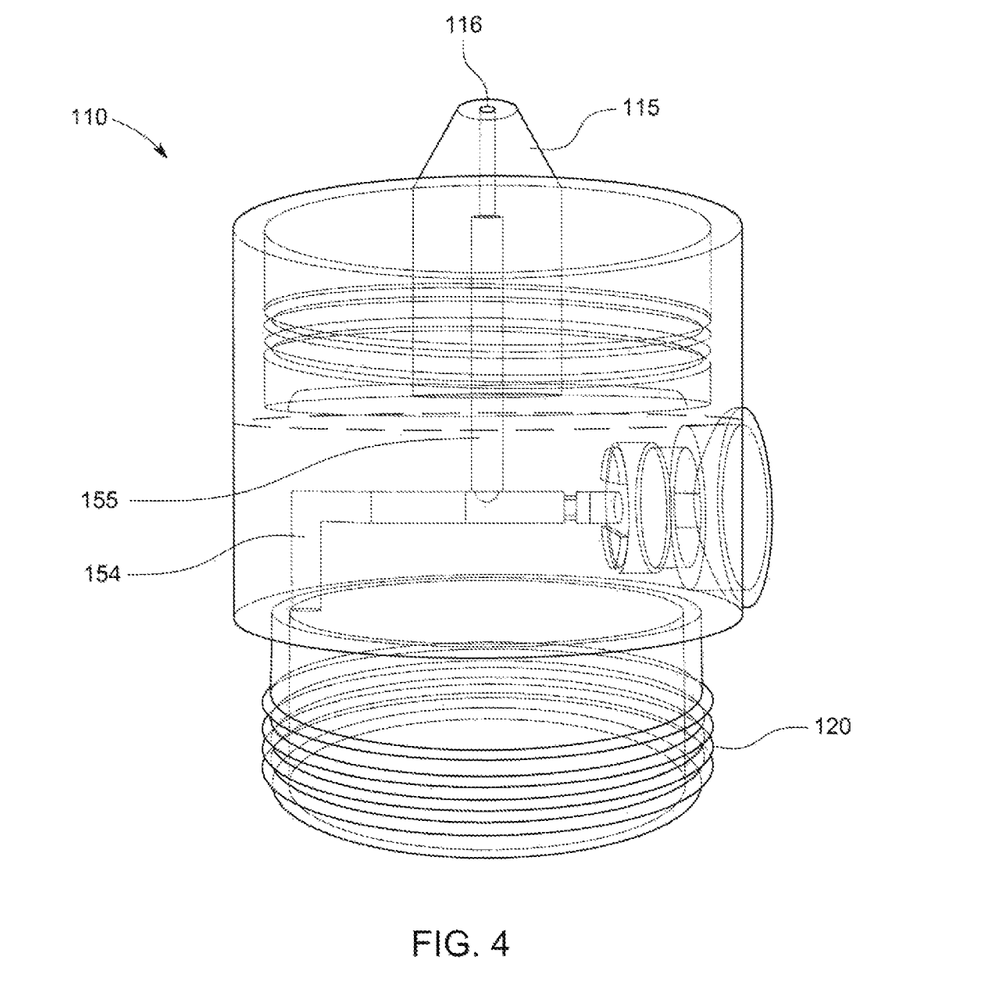
FIG. 4 is a side cutaway view of the main body of the lube distribution apparatus shown in FIG. 3.
Figure 5:
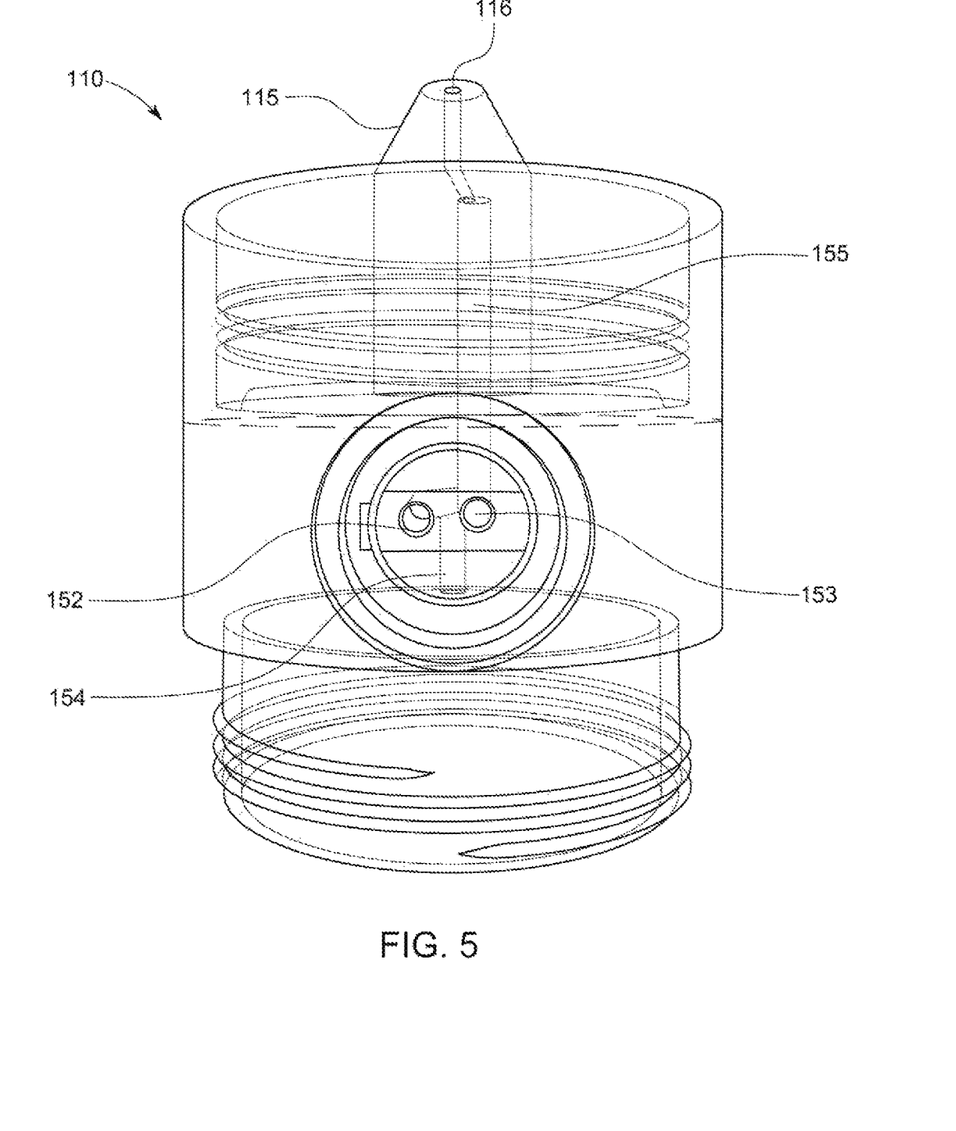
FIG. 5 is a front cutaway view of the main body of the lube distribution apparatus shown in FIG. 3.
Figure 6:
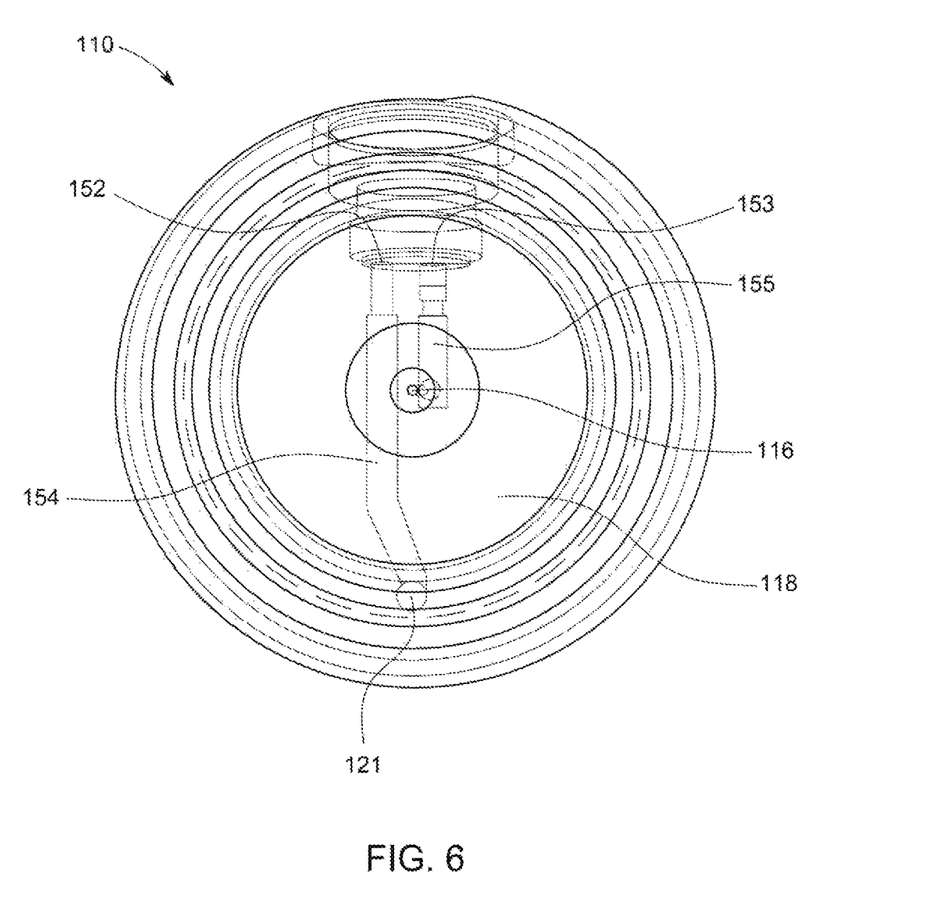
FIG. 6 is a bottom cutaway view of the main body of the lube distribution apparatus shown in FIG. 3.
Figure 7:
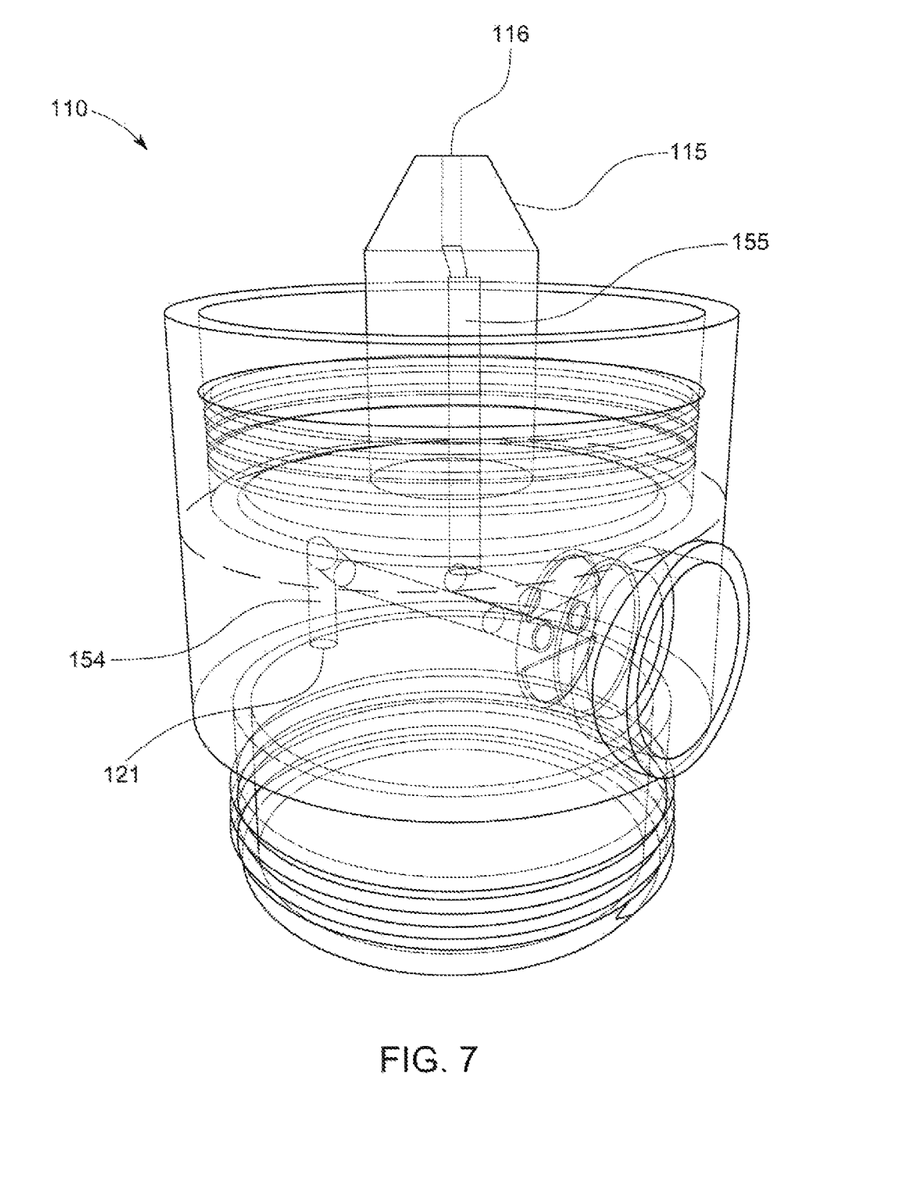
FIG. 7 is a perspective cutaway view of the main body of the lube distribution apparatus shown in FIG. 3.

As best shown in FIG. 3, one presently preferred embodiment of the invention comprises a lube distribution apparatus 100 for use in connection with a sperm collection device 10 as shown in FIG. 1 and FIG. 2. The lube distribution apparatus 100 is configured to be installed on the sperm collection device 10 in lieu of the end cap 13. The lube distribution apparatus 100 is comprised of three primary components—a main body 110, an end cap 130 and a primer purge pump assembly 150.

The main body 110 is shaped in such a way as to make it easily attachable to the sperm collection device. In the case of the flashlight shaped device shown in FIG. 1 and FIG. 2, the main body 110 is similarly cylindrically shaped. A first end of the main body 110 is provided with a cylindrical opening 111 having a bottom 112 and sidewall 113. The inner surface of the sidewall 113 is provided with threads 114 that are sized and configured to engage threads on the small end 15 of the sperm collection device 10 in place of the end cap 13. An injection tip 115 extends upwardly from the bottom 112 and has an opening 116 therein through which lubricant is injected into the interior portion of the sperm collection device 10. The second end of the main body 110 is similarly provided with a cylindrical opening 117 having a bottom 118 and sidewall 119 that forms a reservoir for holding lubricant. The outer surface of the sidewall 119 is provided with threads 120 that are sized and configured to engage threads 132 associated with the end cap 130. An opening 121 is provided in the bottom 118 of the lubricant reservoir for transferring lubricant from the lubricant reservoir through the primer purge pump assembly 150 and out of the opening 116 in the injection tip 115 into the interior of the sperm collection device 10.

Figure 8:
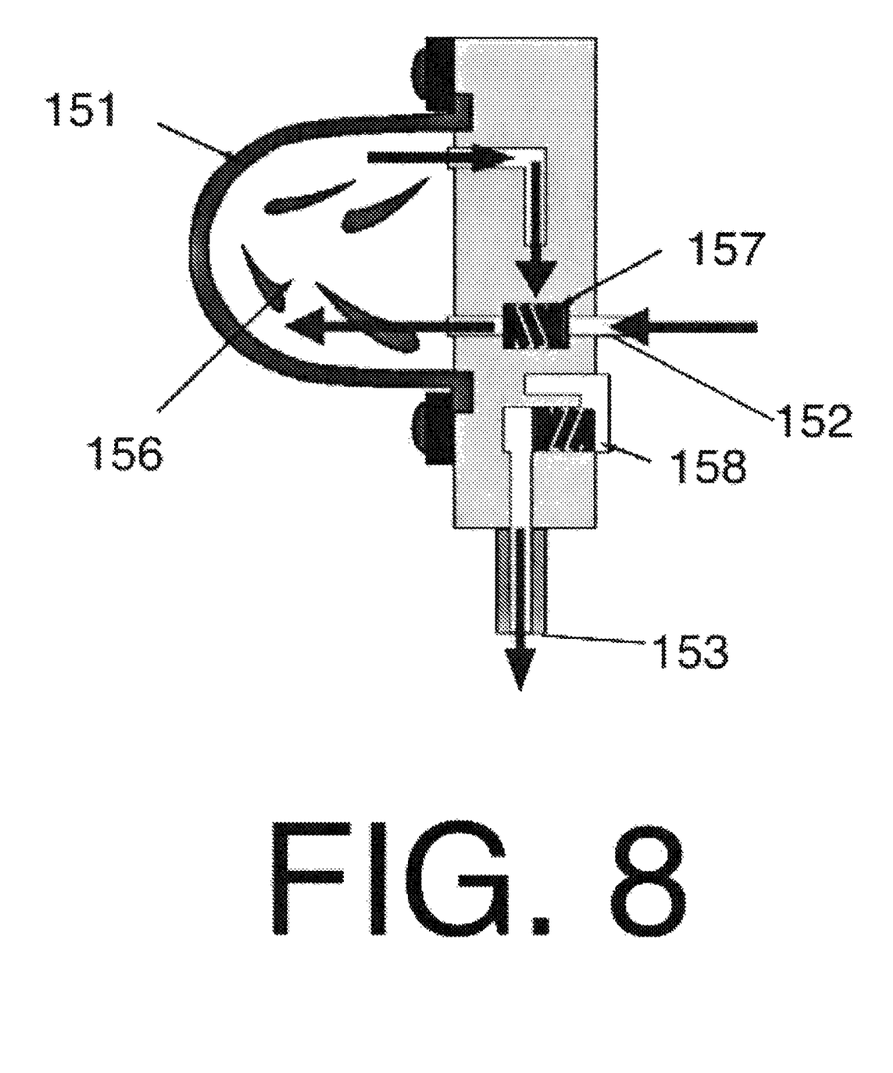
FIG. 8 is a side cutaway view of a portion of the primer purge pump assembly of the lube distribution apparatus shown in FIG. 3.

The primer purge pump assembly 150 controls the flow of lubricant from the lubricant reservoir into the interior of the sperm collection device 10. The primer purge pump assembly 150 includes a primer purge pump 151 having an inlet opening 152 and an outlet opening 153. The inlet opening 152 is in fluid communication with the opening 121 in the lubricant reservoir via inlet passageway 154. Similarly, the outlet opening 153 is in fluid communication with the opening 116 in the injection tip 115 via outlet passageway 155. As best shown in FIG. 8, the primer purge pump 151 is comprised of a purge bulb 156, an inlet check valve 157 associated with the inlet opening 152, and an outlet check valve 158 associated with the outlet opening 153. When the purge bulb 156 is depressed, the outlet check valve 158 opens and lubricant is forced through the outlet check valve 158 and outlet opening 153 and into the outlet passageway 155. When the purge bulb 156 is released, the outlet check valve 158 closes and the inlet check valve 157 opens to draw lubricant from the lubricant reservoir through the inlet passageway 154. A vacuum is created by the expanding bulb drawing the lubricant from the lubricant reservoir through the inlet passageway 154 into the purge bulb 156. The inlet check valve 157 and outlet check valve 158 may be any type of check valve known in the art, such as a ball valve, diaphragm check valve, swing check valve, stop-check valve, lift-check valve in-line check valve, and the like. According to one preferred embodiment of the invention, a Schrader valve is used. A Schrader valve is a check valve that allows flow in one direction, and is used in almost every car and bike tire in the world. It is a normally closed valve that usually holds in air. However, in the present invention, the Schrader valve it is used to relieve vacuum that is created in the lubricant reservoir from fluid being sucked into the inlet 152 and to the primer bulb 156.

The end cap 130 attaches to the main body 110 to close and assist in sealing off the the lubrication reservoir to the atmosphere. The end cap according to one presently preferred embodiment is cylindrically shaped. A first end of the end cap 130 is provided with a cylindrical opening 131 having a bottom 133 and sidewall 134. The inner surface of the sidewall 133 is provided with threads 132 that are sized and configured to engage threads 120 on the outer surface of the sidewall 119 of the main body 110 thereby closing and sealing the lubrication reservoir. The end cap 130 can be removed to make it easy to clean the lubricant reservoir when done with the device or for changing out the lube for a different type of lube. With the end cap 130 removed, different attachments can be put in its place. (i.e. shower mount).

Figure 9:
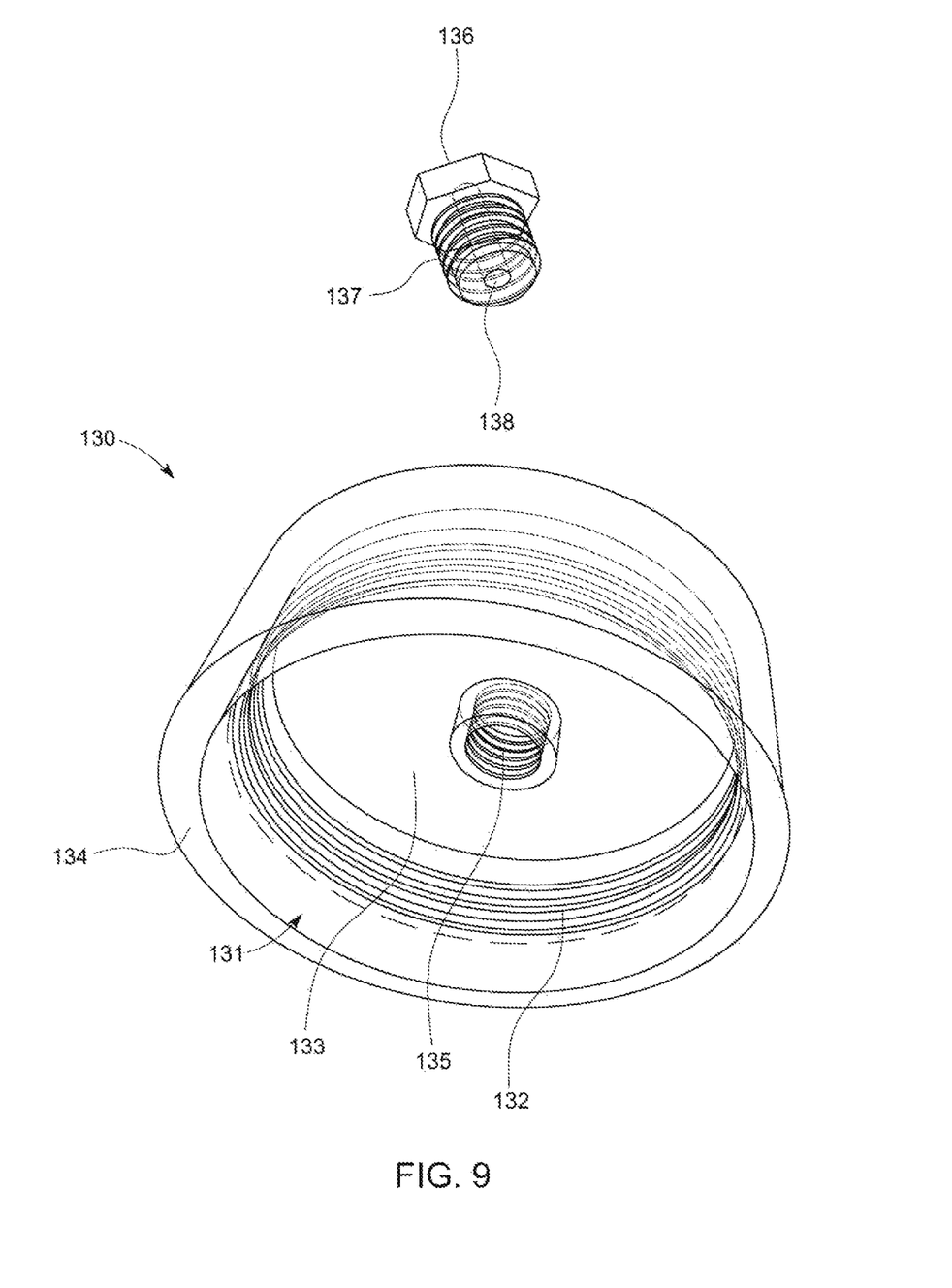
FIG. 9 is a perspective view of an end cap assembly according to an alternative embodiment of the present invention.

An alternative embodiment of an end cap 130 is shown in FIG. 9. According to this embodiment, a threaded opening 135 is provided in the bottom 133 of the end cap 130. A bushing 136 having threads 137 on the outer surface thereof is provided for selectively closing and sealing the threaded opening 135. The bushing 136 also has an attaching feature to hold a Schrader valve 138 with a sealing surface between them. The bushing 136 can be removed so that lube can be added to the lubricant reservoir easily without having to remove the end cap 130 to expose all of the fluid inside the reservoir and making it more likely to spill the lube.

The primary purpose of this invention is to transfer a predetermined amount of fluid lubricant from a lubricant reservoir and have the fluid travel throughout this main body 110 to the injection tip 115 and into the sperm collection device where lubrication is needed and as needed decided by the user.

The process starts at the lubricant reservoir, where lubrication is held and ready to use when needed. The lubrication reservoir is connected to the primer bulb 156 thru an inlet passageway 154 that is located inside of the main body 110. The opening 121 for the inlet passageway is located in the bottom 118 of the lubricant reservoir on the opposite side from the primer bulb 156. When the lube distribution apparatus 100 is held in its proper position with the primer bulb 156 facing up, fluid on the inside of the lubrication reservoir will begin to collect at the bottom side of the main body 110 from the forces of gravity, pooling the fluid at the opening 121 of the inlet passageway 154, where fluid will constantly be ready to go.

When the primer bulb 156 is released, it creates a vacuum from the retraction of the bulb as it returns to its normal state. With the vacuum created it pulls the inlet check valve 157 open and sucks in lubrication thru the inlet passageway 154 from the lubricant reservoir. Once the fluid has been pulled from the reservoir thru the inlet passageway 154 and past the inlet check valve 157, it will arrive at the inside of the push bulb 156, where it will sit until the push bulb 156 is depressed. When the push bulb 156 is depressed, it will create pressure inside the primer bulb 156, thereby pushing the fluid through the outlet check valve 158 and through the outlet passageway 155 until it reaches the opening 116 in the injection tip 115, squirting fluid into the center of the sperm collection device 10 where lubrication is needed.

The opening 116 in the injection tip 115 is smaller in diameter than the outlet passageway 155, so that when the pressurized fluid is traveling and reaches the injection tip 115, the pressure will increase further due to a restriction cause by the smaller diameter passageway in the injection tip 115. This allows the lube distribution apparatus 100 to squirt a more precise stream of fluid while having enough pressure to squirt out further to reach the lubricant's destination.

The end cap 130 is used to hold the fluid inside the lubrication reservoir so no leakage can occur. The end cap 130 also houses the bushing 136 that houses the Schrader valve 138 inside it. The purpose of the bushing 136 is to house the Schrader valve 138 and to be removable from the end cap 130. The Schrader valve 138 is a normal closed check valve. It's purpose for this device is to relieve vacuum that is created in the lubricant reservoir. When the fluid from inside the lubricant reservoir is in the process of being sucked into the opening 121 of the inlet passageway 154, it will create a vacuum inside the lubricant reservoir. When enough vacuum is created inside the lubricant reservoir, it will overcome the force of the spring that keeps the Schrader valve 138 in its normal closed position.

Figure 10:
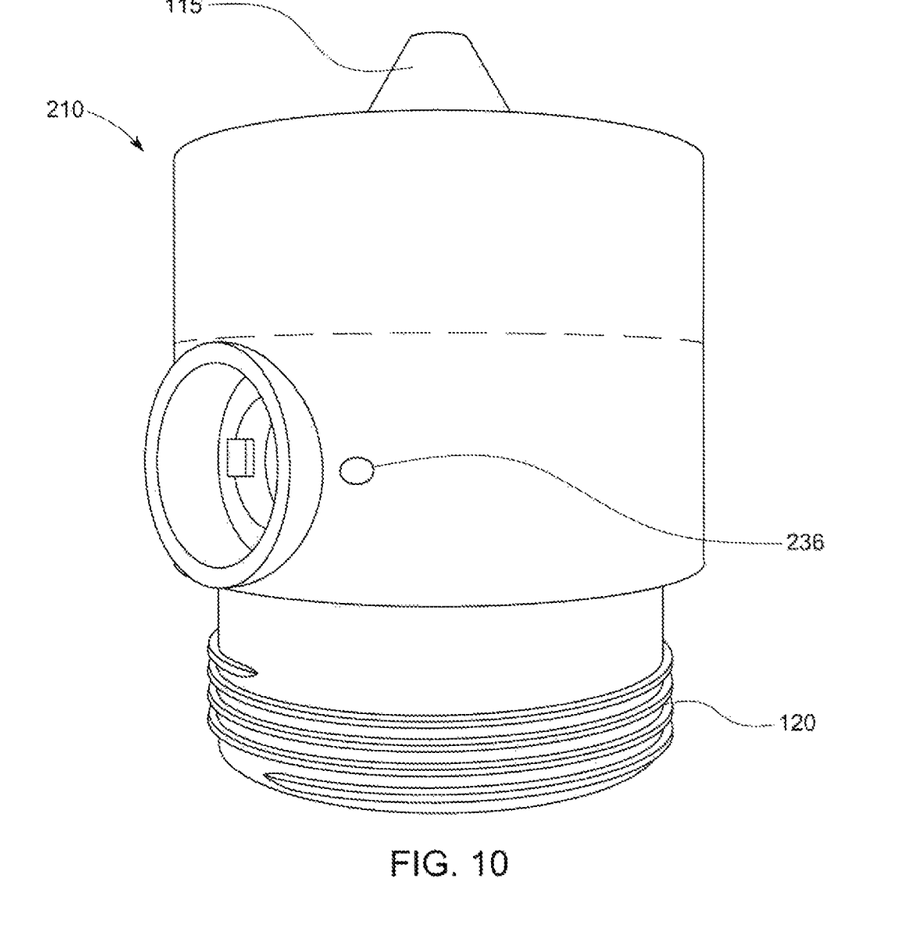
FIG. 10 is a side perspective view of the main body of a lube distribution apparatus according to an alternative preferred embodiment of the invention.
Figure 11:
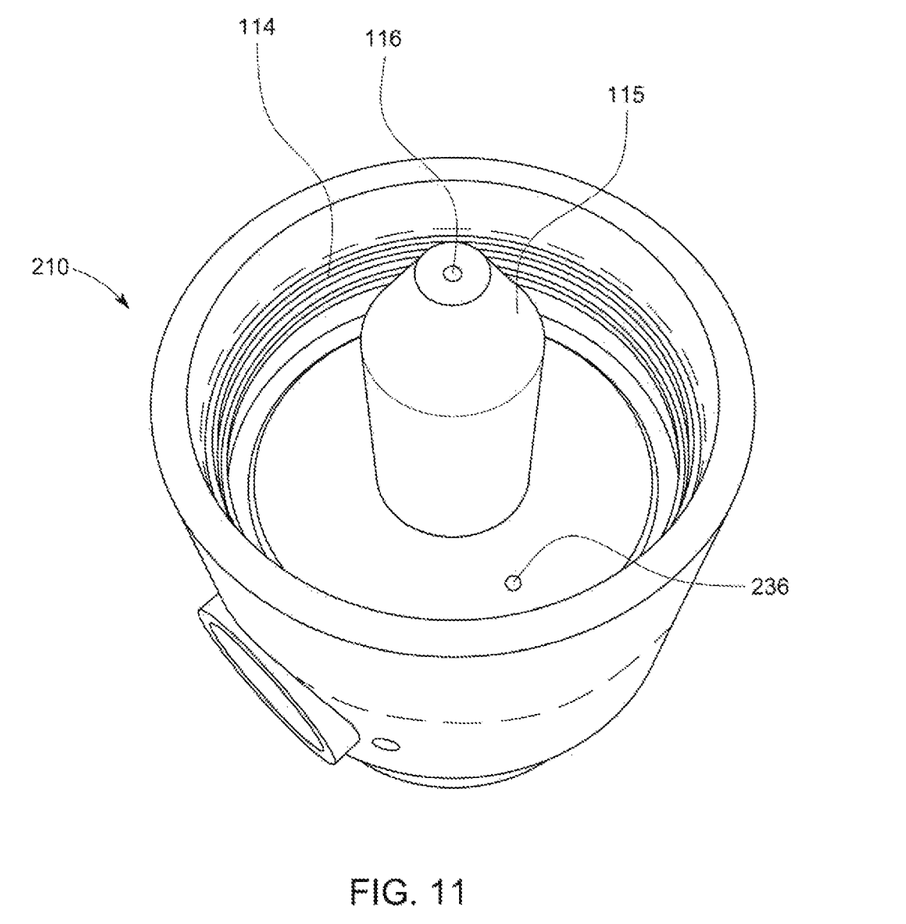
FIG. 11 is a top perspective view of the main body of the lube distribution apparatus shown in FIG. 10.
Figure 12:
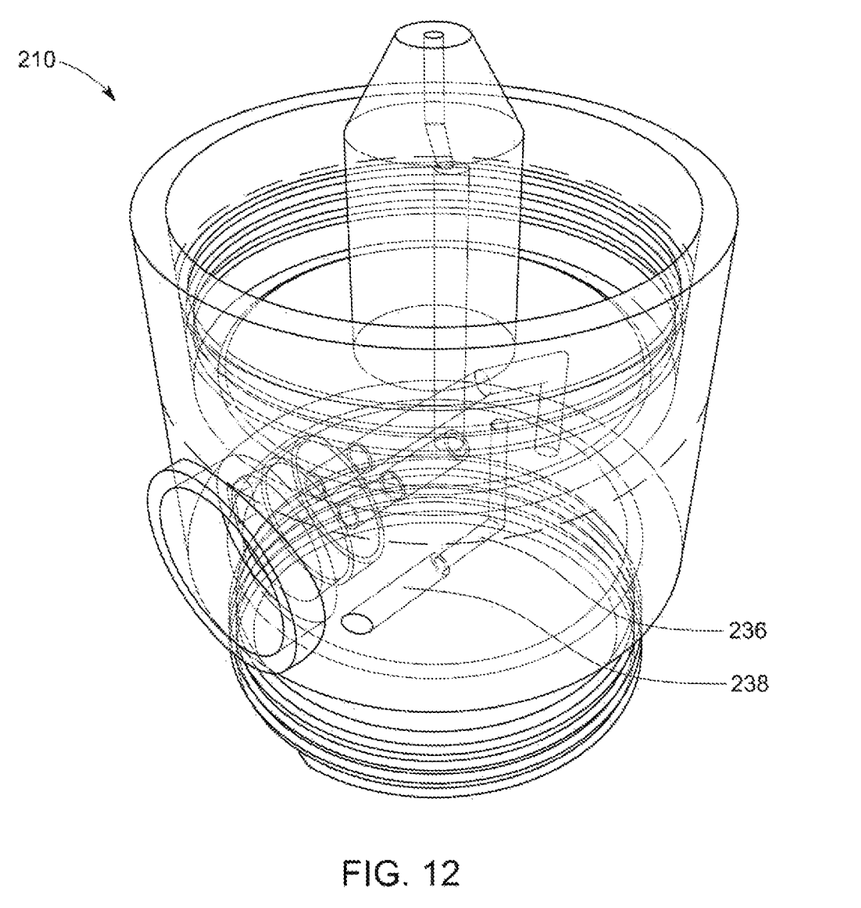
FIG. 12 is a perspective cutaway view of the main body of the lube distribution apparatus shown in FIG. 10.

FIG. 10-FIG. 12 show the main body 210 a lube distribution apparatus according to an alternative embodiment. With a few exceptions, which are noted here, the main body 210 and lube distribution apparatus of the alternative embodiment are the same as the first embodiment, with like reference numerals indicating like components. However, rather than having a vented end cap as shown in FIG. 9, the alternative embodiment of the main body 210 includes an integrally formed vent 236. The vent includes a normally closed Schrader check valve 238 to relieve vacuum that is created in the lubricant reservoir. The need to vent the fluid reservoir from the main body 210 rather than the end cap 130 arises where additional attachments or accessories (i.e. a shower mount) are attached to the threaded end of the main body instead of the cap. As these accessories typically are not vented, there is a need to vent the reservoir from somewhere other than the end cap, which is no longer used. Relocating the vent 236 into the main body 210 allows venting regardless of the attachments or accessories installed.

Seals such as o-rings and rubber or plastic gaskets as are commonly known in the art can be used between the various components of the lube distribution apparatus 10 to seal leaks and prevent fluid from escaping where it is not intended.

This detailed description, and particularly the specific details of the exemplary embodiment disclosed, is given primarily for clearness of understanding and no unnecessary limitations are to be understood therefrom, for modifications will become evident to those skilled in the art upon reading this disclosure and may be made without departing from the spirit or scope of the claimed invention.

The invention claimed is:

1. A lube distribution apparatus for use in connection with a sperm collection device and configured to be installed on the sperm collection device, said lube distribution apparatus comprising:
   a main body having a cylindrical opening at a first end thereof, said cylindrical opening having means for engaging an open end of the sperm collection device,
   a lubricant reservoir located within said main body for housing lubricant to be used in the sperm collection device;
   a first opening in said main body in fluid communication with the lubricant reservoir;
   an injector tip projecting from the first end of the main body, said injector tip having a second opening therein;
   a first fluid passageway connecting said first opening in said main body to an inlet opening in a primer purge pump; and
   a second fluid passageway connecting said second opening in the injector tip to an outlet opening in said primer purge pump; and
   wherein said primer purge pump further comprises a purge bulb covering said inlet opening and said outlet opening creating a compressible chamber in fluid communication with said inlet opening and said outlet opening.

2. The lube distribution apparatus of claim 1 further comprising an end cap removably affixed to a second end of said main body and enclosing said lubricant reservoir.

3. The lube distribution apparatus of claim 1 wherein the primer purge pump further comprises:
   an inlet check valve associated with said inlet opening;
   an outlet check valve associated with said outlet opening.

4. The lube distribution apparatus according to claim 1 further comprising a vent for allowing outside air to enter the lubricant reservoir.

5. The lube distribution apparatus according to claim 4 further comprising an end cap removably affixed to a second end of said main body and enclosing said lubricant reservoir, said vent located in said end cap.

6. The lube distribution apparatus according to claim 5 wherein said vent further comprises an opening in the cap that exposes an interior of the lubricant reservoir to outside air, and a check valve located in said opening in the cap to control the flow of air from outside into the lubricant reservoir.

7. The lube distribution apparatus according to claim 6 wherein the check valve is a Schrader valve.

8. The lube distribution apparatus according to claim 6 wherein said vent is disposed in a bushing that is removably secured to an opening in said end cap.

9. The lube distribution apparatus according to claim 4 wherein said vent further comprises an opening in an outer surface of the main body in fluid communication with the outside air, an opening in fluid communication with the lubricant reservoir; a fluid passage connecting the first opening to the second opening; and a check valve located in said opening in the outer surface of the main body to control the flow of air from outside into the lubricant reservoir.

10. The lube distribution apparatus according to claim 9 wherein the check valve is a Schrader valve.

\* \* \* \* \*